(12) United States Patent
Qi et al.

(10) Patent No.: US 8,197,500 B2
(45) Date of Patent: *Jun. 12, 2012

(54) BIOLOGICAL MEMBRANE-CARRYING ANEURYSM CLIP

(75) Inventors: Song-Tao Qi, Guangzhou (CN); Guo-Feng Xu, Guangzhou (CN)

(73) Assignee: Grandhope Biotech Co., Ltd. (CN)

( * ) Notice: Subject to any disclaimer, the term of this patent is extended or adjusted under 35 U.S.C. 154(b) by 230 days.

This patent is subject to a terminal disclaimer.

(21) Appl. No.: 11/497,097

(22) Filed: Aug. 1, 2006

(65) Prior Publication Data

US 2007/0032806 A1 Feb. 8, 2007

(30) Foreign Application Priority Data

Aug. 4, 2005 (CN) .......................... 2005 1 0036315

(51) Int. Cl.
*A61B 17/08* (2006.01)
(52) U.S. Cl. ........................... 606/157; 606/151; 602/48
(58) Field of Classification Search .................. 606/151, 606/157, 158; 602/48; 424/422, 423, 424, 424/520, 522
See application file for complete search history.

(56) References Cited

U.S. PATENT DOCUMENTS

| 3,802,437 | A | * | 4/1974 | Kees, Jr. ........................ 606/142 |
| 3,974,526 | A | | 8/1976 | Dardik et al. |
| 4,083,066 | A | | 4/1978 | Schmitz et al. |
| 4,319,363 | A | | 3/1982 | Ketharanathan |
| 4,481,009 | A | | 11/1984 | Nashef |
| 4,597,766 | A | | 7/1986 | Hilal et al. |
| 4,765,335 | A | | 8/1988 | Schmidt et al. |
| 4,793,344 | A | | 12/1988 | Cumming et al. |
| 5,067,962 | A | | 11/1991 | Campbell et al. |
| 5,078,744 | A | | 1/1992 | Chvapil |
| 5,080,670 | A | | 1/1992 | Imamura et al. |
| 5,217,492 | A | | 6/1993 | Guire et al. |
| 5,290,217 | A | * | 3/1994 | Campos .......................... 600/37 |
| 5,416,074 | A | * | 5/1995 | Rabaud et al. .................. 514/21 |
| 5,447,536 | A | | 9/1995 | Girardot et al. |
| 5,549,666 | A | | 8/1996 | Hata et al. |

(Continued)

FOREIGN PATENT DOCUMENTS

CN  1093566  10/1994

(Continued)

OTHER PUBLICATIONS

IPR—PCT/CN2006/003419.

(Continued)

*Primary Examiner* — Corrine M McDermott
*Assistant Examiner* — Alexander Orkin
(74) *Attorney, Agent, or Firm* — Raymond Sun

(57) ABSTRACT

An aneurysm clip has a biological membrane and a metal clip. The membrane is harvested from an animal, crosslinked, and then has its antigens minimized. The membrane also has an active layer coupled thereto. The metal clip has a first clip bar and a second clip bar that are attached to each in a biased manner, a first clip arm that extends perpendicularly from the second clip bar, and a second clip arm that extends perpendicularly from the first clip bar. A first end of the biological membrane is coupled to the first clip arm, and a second end of the biological membrane is coupled to the second clip arm in a manner that defines a receiving portion.

8 Claims, 2 Drawing Sheets

U.S. PATENT DOCUMENTS

| | | |
|---|---|---|
| 5,733,339 A | 3/1998 | Girardot et al. |
| 5,741,283 A * | 4/1998 | Fahy .......................... 606/157 |
| 5,758,420 A * | 6/1998 | Schmidt et al. ............. 29/896.9 |
| 5,891,196 A | 4/1999 | Lee et al. |
| 5,902,338 A | 5/1999 | Stone |
| 5,955,110 A | 9/1999 | Patel et al. |
| 5,976,192 A | 11/1999 | McIntyre et al. |
| 5,984,858 A | 11/1999 | Stone |
| 6,008,292 A | 12/1999 | Lee et al. |
| 6,063,120 A | 5/2000 | Stone |
| 6,090,995 A | 7/2000 | Reich et al. |
| 6,106,555 A | 8/2000 | Yang |
| 6,117,979 A | 9/2000 | Hendriks et al. |
| 6,177,514 B1 | 1/2001 | Pathak et al. |
| 6,241,981 B1 | 6/2001 | Cobb et al. |
| 6,251,117 B1 * | 6/2001 | Kringel et al. ................ 606/158 |
| 6,458,889 B1 | 10/2002 | Trolisas et al. |
| 6,482,584 B1 | 11/2002 | Mills et al. |
| 6,572,650 B1 | 6/2003 | Abraham et al. |
| 7,053,051 B2 | 5/2006 | Hendriks et al. |
| 7,060,103 B2 | 6/2006 | Carr, Jr. et al. |
| 7,077,851 B2 * | 7/2006 | Lutze et al. ................... 606/158 |
| 7,674,289 B2 * | 3/2010 | Xu ............................. 623/13.17 |
| 7,820,871 B2 * | 10/2010 | Xu ................................... 602/48 |
| 2001/0031743 A1 | 10/2001 | Peterson et al. |
| 2001/0044654 A1 | 11/2001 | Chen et al. |
| 2002/0042473 A1 | 4/2002 | Trolisas et al. |
| 2002/0081564 A1 | 6/2002 | Levy et al. |
| 2002/0091445 A1 | 7/2002 | Sung et al. |
| 2002/0095218 A1 | 7/2002 | Carr |
| 2002/0099448 A1 | 7/2002 | Hiles et al. |
| 2002/0103542 A1 * | 8/2002 | Bilbo ......................... 623/23.72 |
| 2002/0138152 A1 | 9/2002 | Francis et al. |
| 2003/0013989 A1 | 1/2003 | Obermiller et al. |
| 2004/0038257 A1 | 2/2004 | Ishii et al. |
| 2004/0202625 A1 | 10/2004 | Daniloff et al. |
| 2005/0119736 A1 | 6/2005 | Zilla et al. |
| 2005/0136543 A1 * | 6/2005 | Torres et al. ..................... 436/34 |
| 2005/0187140 A1 | 8/2005 | Hunter et al. |
| 2005/0229323 A1 | 10/2005 | Mills et al. |
| 2008/0195229 A1 | 8/2008 | Quijano et al. |

FOREIGN PATENT DOCUMENTS

| | | |
|---|---|---|
| CN | 1445003 | 5/1999 |
| CN | 1237889 | 12/1999 |
| CN | 1267201 | 9/2000 |
| CN | 1313741 | 9/2001 |
| CN | 1330528 | 1/2002 |
| CN | 1456363 | 11/2003 |
| CN | 1473551 | 2/2004 |
| CN | 1556715 | 12/2004 |
| CN | 1579342 | 2/2005 |
| CN | 1903144 | 1/2007 |
| CN | 101172165 | 5/2008 |
| EP | 0965310 | 12/1999 |
| EP | 1112725 | 7/2001 |
| JP | 6-319744 | 11/1994 |
| JP | 2003-513682 | 4/2003 |
| JP | 2003-531685 | 10/2003 |
| WO | WO9417851 | 8/1994 |
| WO | WO 9822158 | 5/1998 |
| WO | WO00/13612 | 3/2000 |
| WO | WO00/35374 | 6/2000 |
| WO | WO 0032250 | 6/2000 |
| WO | WO0232327 | 4/2002 |

OTHER PUBLICATIONS

IPR—PCT/CN2006/003442.
IPR—PCT/CN2006/003443.
IPR—PCT/CN2006/003444.
IPR—PCT/CN2006/001878.
IPR—PCT/CN2006/001879.
IPR—PCT/CN2006/001880.
2005100361744 dated May 22, 2009.
2005100361795 dated May 22, 2009.
2005100363152 dated 2000.
2005101207946 dated Jun. 2009.
2005101207912 dated Jul. 2009.
2005101207965 dated Sep. 2009.
2005101207927 dated Sep. 2009.
200810029656.0 dated Aug. 2011.
200810029653.7 dated Sep. 2010.

* cited by examiner

BIOLOGICAL MEMBRANE-CARRYING ANEURYSM CLIP

BACKGROUND OF THE INVENTION

1. Field of the Invention

The present invention relates to a medical prosthesis for human implantation, and in particular, to an aneurysm clip for treating aneurysms.

2. Description of the Prior Art

Aneurysms are one of the most common vascular disorders. There are many treatment methods for aneurysm, but for an aneurysm of a certain morphology, using an aneurysm clip to clip the aneurysm cyst at the root (i.e., at the location parallel to the vascular wall) and to close the cyst is a simple treatment method which is particularly suitable for locations that are difficult to access. This method has been applied in clinical treatment for some time and the short term efficacy is very good. However, because the other side of the vascular wall perpendicular to the axis also becomes thinner due to elongation when the aneurysm is formed, closing one side of the aneurysm can make the other side even thinner and result in the risk that a new aneurysm might develop, thereby resulting in a less-than ideal treatment result. In addition, a conventional aneurysm clip is not effective for fusiform aneurysms.

In light of the above reasons, there still remains a need for an aneurysm clip which overcomes the drawbacks mentioned above.

SUMMARY OF THE DISCLOSURE

It is an object of the present invention to provide a biological membrane-carrying aneurysm clip that has a durable biological membrane which can wrap the outer circumference of the clipped blood vessel.

It is an object of the present invention to provide a biological membrane-carrying aneurysm clip that prevents further formation of aneurysms at the treatment location, and that prevents breakage of the thinner vessel wall.

It is another objective of the present invention to provide a method of preparing the biological membrane-carrying aneurysm clip.

In order to accomplish the objects of the present invention, the present invention provides an aneurysm clip having a biological membrane and a metal clip. The membrane is harvested from an animal, crosslinked, and then has its antigens minimized. The membrane also has an active layer coupled thereto. The metal clip has a first clip bar and a second clip bar that are attached to each in a biased manner, a first clip arm that extends perpendicularly from the second clip bar, and a second clip arm that extends perpendicularly from the first clip bar. A first end of the biological membrane is coupled to the first clip arm, and a second end of the biological membrane is coupled to the second clip arm in a manner that defines a receiving portion.

DETAILED DESCRIPTION OF THE PREFERRED EMBODIMENTS

Figure 1:
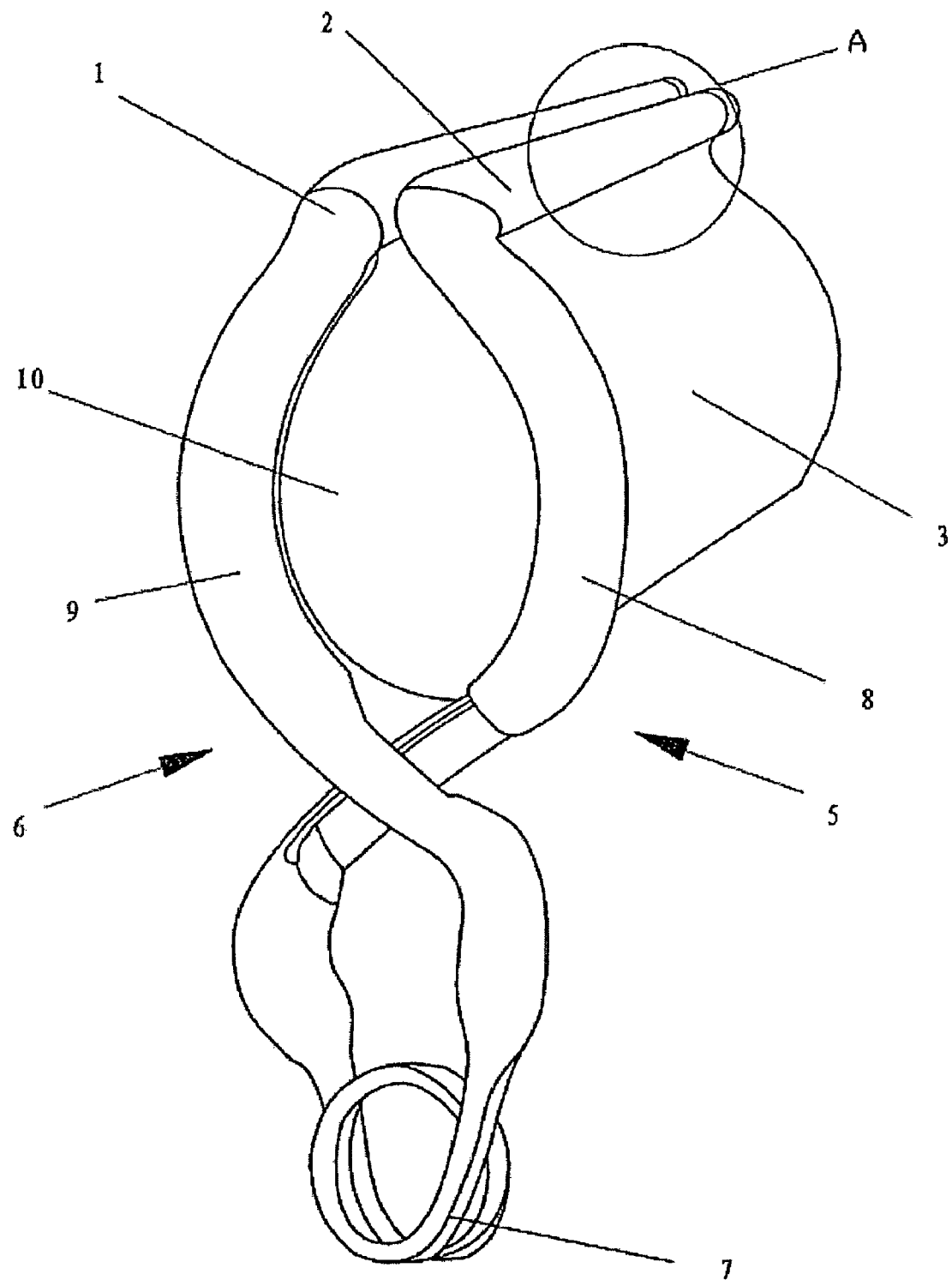
FIG. 1 is a perspective view of an aneurysm clip according to one embodiment of the present invention.

The following detailed description is of the best presently contemplated modes of carrying out the invention. This description is not to be taken in a limiting sense, but is made merely for the purpose of illustrating general principles of embodiments of the invention. The scope of the invention is best defined by the appended claims.

The present invention provides a biological membrane-carrying aneurysm clip that has a metal clip and a biological membrane. The metal clip is made of medical stainless steel or titanium alloys, and has a cross-lapping first clip bar and second clip bar, with the ends of the clip bars connected through a spring device. A first clip arm and a second clip arm are provided at the end of the half slip ring on the first clip bar and the end of the half slip ring on the second clip bar, respectively. The two ends of the biological membrane are connected to the first clip arm and the second clip arm, respectively, to form a membrane sheath. The biological membrane can be selected from porcine, bovine or ovine pleura, peritoneum, pericardium or small intestine submucosa, then prepared by crosslinking and fixation with a fixative, treated to minimize antigens, and then coated with a surface layer containing an active layer.

Animal tissues are easily degraded or decomposed by microorganisms, so that crosslinking and fixation with a fixative is required. Conventionally, glutaraldehyde is utilized as a fixative, but glutaraldehyde produces toxic radicals. However, aldehydes undergo crosslinking with proteins through the acetal reaction and toxic aldehydes are released when the crosslinked products are degraded, so that products fixed with an aldehyde have long-term residual toxicity. When epoxides, diamides, diisocyanates or carbodiimides are utilized as fixatives in place of aldehydes, this toxicity problem can be eliminated. When an epoxide is utilized, for example, proteins are crosslinked through a ring opening reaction of the epoxide, and reverse ring closure to form the epoxide back does not readily occur, and the degradation products are diols and polyols which can be metabolized by the body so that there is no risk of toxic aldehyde radicals. The stability of the animal tissues after treatment is also higher than those fixed with aldehydes. According to modern immunological theory, the antigenicity of animal tissues stems mainly from active groups located at specific sites and in specific conformations, and these active groups include —OH, —NH2, —SH, etc. The specific conformations result mainly from some specific hydrogen bonding formed by spiral protein chains. The specific sites and conformations are called antigen determinants. When treating the animal ligaments, one or several small, active reagents (e.g., acid anhydrides, acid chlorides, acylamides, epoxides, etc.) which can readily react with these groups are used to bind and block these groups, which in turn effectively minimizes the antigenicity, and in the meantime strong hydrogen bonding reagents (e.g., guanidine compounds) are utilized to form new hydrogen bonds and replace the inherent hydrogen bonding of the specific conformations, which changes the specific conformations and further effectively minimizes the antigenicity. The structure of the animal membranes cannot be easily altered after they have been crosslinked and fixed by non-aldehyde fixatives such as epoxides, and the tissues are not easily degraded or decomposed, and collagenase only begins to phagocytize and degrade them due to the synergistic effect of fibrinolysin and kallikrein released by nascent tissues, which means that the new ligament tissues have sufficient time to grow and take hold, while no toxic radicals remain. The immunogenicity is effectively minimized by blocking the active groups in the proteins and changing the conformation, and the resulting membrane has no chronic immune rejection while having excellent biocompatibility. When applying the biological membrane-carrying aneurysm clip, the circumference of the blood vessel at the clipped site is wrapped by the membrane, and the biological membrane and the outer membrane of the blood vessel can grow together, resulting in biological strengthening of the blood vessel and excellent treatment efficacy.

Furthermore, the tissue compatibility is improved by modifying the surface by incorporating an active component (as described below), including a specific polypeptide and glucosaminoglycan. One example of the polypeptide is the polypeptide consisting of 16 lysines (K16), glycine (G), arginine (R), asparatic acid (D), serine (S), proline (P) and cysteine (C), and the glucosaminoglycans are hyaluronic acid, chondroitin sulfate, dermatan sulfate, heparin, acetylated heparin sulfate and keratan sulfate. These active components are beneficial in facilitating growth of the cells on the wall of the wrapped blood vessel and fusing with the wall of the blood vessel, enhancing the bio-strength.

Method

A method of preparing the biological membrane-carrying aneurysm clip according to the present invention comprises the following steps, wherein the biological membrane utilizes natural durable tissues from animals:

1. Pretreatment: Initial sterilization is performed using a broad spectrum, highly-effective, low-toxicity bacteriacide, followed by trimming irregular portions.

2. Defatting: The fatty substances in the membrane are extracted with organic solvents using known tissue-treatment techniques.

3. Cross-linking and Fixation: The protein molecules in the membrane are crosslinked and fixed using a fixative, as described in greater detail hereinbelow.

4. Minimizing antigens: An active reagent is utilized to block the specific active groups such as —OH, —NH2, —SH, etc., in the proteins of the membrane, and a reagent with strong hydrogen bonding power is utilized to replace the specific hydrogen bonding in the spiral chains of the protein molecules in the membrane and alter its specific conformation.

5. Coupling of active layer: An active surface layer containing a specific polypeptide or glucosaminoglycan capable of adhering to growth factors is incorporated on the surface of the membrane through crosslinking and coupling using a coupling agent.

6. The two ends of the obtained biological membrane are fixed on the clip arms of the metal clip respectively using a medical adhesive.

Broad Spectrum Antibacterial Agents

The broad spectrum antibacterial agents in step 1 of the above method can be selected among benzalkonium bromide, sodium azide and chlorhexidine.

Organic Solvents

The organic solvents in step 2 of the above method can be selected among chloroform, ethyl acetate, anhydrous alcohol and mixtures thereof.

Fixative

The fixative applied in step 3 of the above method may be an epoxy compound that has a hydrocarbon backbone, that is water-soluble, and which does not contain an ether or ester linkage in its backbone. This fixative is described in U.S. Pat. No. 6,106,555, whose entire disclosure is incorporated by this reference as though set forth fully herein. Examples include an epoxide, a diamide, a diisocyanate, or a carbodiimide, in that the epoxide may be a monocyclic epoxide, or a bicyclic epoxide, or it may be a low poly(epoxide) (such as low poly (ethylene oxide), poly(propylene oxide) or a glycidyl ether).

Active Reagents

The active reagents in step 4 of the above method may be low molecular weight organic acid anhydrides, acyl chlorides, acylamides or monocyclic oxides, and the reagents having strong hydrogen bonding power are guanidine compounds.

Active Layer

The active layer in step 5 of the above method can contain a specific polypeptide capable of adhering to and accumulating growth factors, so that angiogenesis can be promoted. Examples of growth factors for blood vessels that can adhere to and accumulate include vascular endothelial growth factor (VEGF), fibroblast growth factor (FGF), platelet-derived growth factor (PDGF-bb) and vascular permeability factor (VPF). One example of the polypeptide is the polypeptide consisting of 16 lysines (K16), glycine (G), arginine (R), aspartic acid (D), serine (S), proline (P) and cysteine (C), and sequence of the composition is K16-G-R-G-D-S-P-C. The glucosaminoglycan can be hyaluronic acid, chondroitin sulfate, dermatan sulfate, heparin, acetylated heparin sulfate or keratin sulfate Coupling Agent for Active Layer The coupling agent utilized for coupling the polypeptide or the glucosaminoglycan in step 5 of the above method may be a diamide, acid anhydride, epoxide, or other bifunctional reagent capable of undergoing a condensation reaction with —NH2, —OH, —COOH, etc.

The present invention provides the following advantages: The aneurysm clip carries a biological membrane having excellent biocompatibility for wrapping the circumference of the blood vessel at the clipped site, which prevents the aneurysm from worsening, and it can grow together with the outer wall of the blood vessel, and thickens and strengthens the biological tissues, and has a good treatment effect with reliable safety.

EXAMPLE 1

Figure 2:
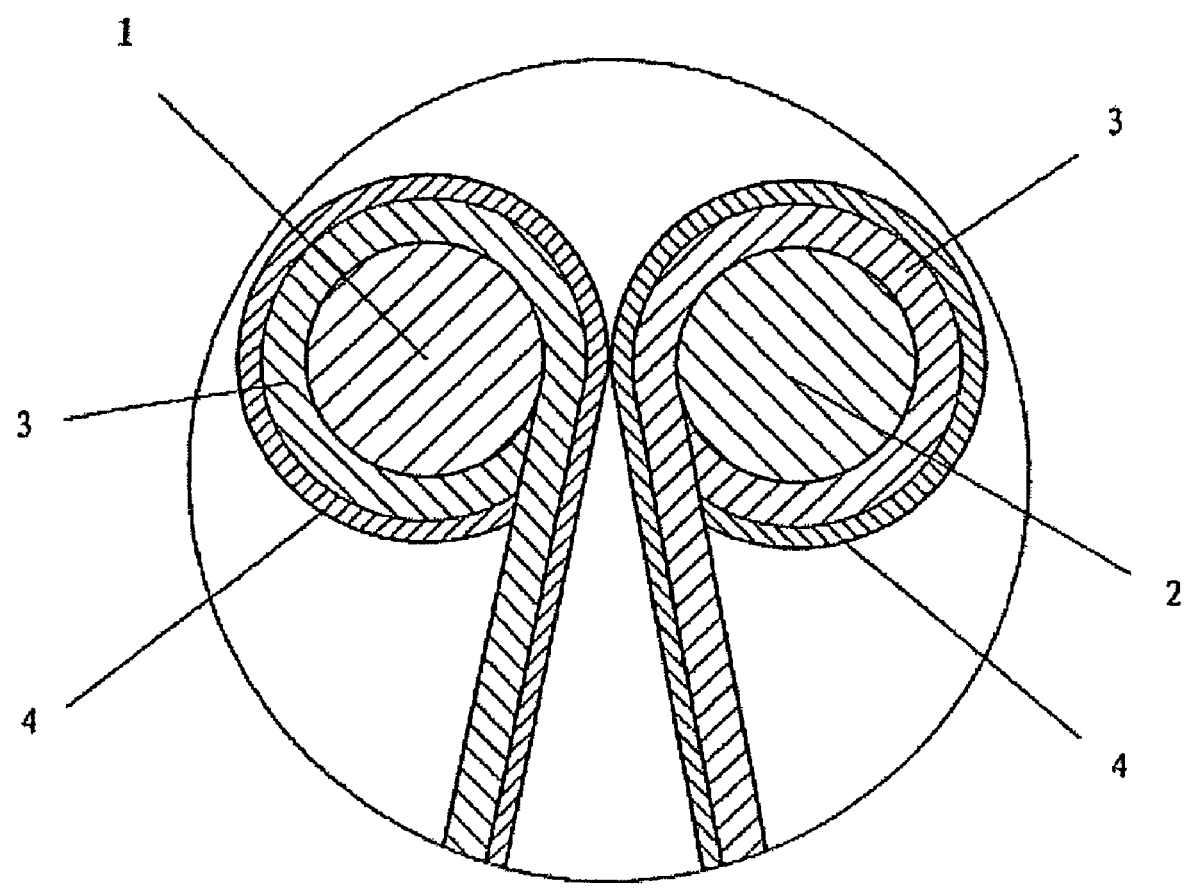
FIG. 2 is a cross-sectional view of the region labeled "A" of the aneurysm clip of FIG. 1.

Referring to FIGS. 1 and 2, the biological membrane-carrying aneurysm clip comprises a metal clip and a biological membrane 3. The metal clip includes a first clip bar 5 and a second clip bar 6 that mutually overlap each other. Each clip bar 5 and 6 can have a shape that looks approximately like the letter "S". One end of each clip bar 5, 6 is connected to each other through a spring device 7. A first clip arm 1 extends perpendicularly from a half slip ring 9 on the other end of the second clip bar 6, and a second clip arm 2 extends perpendicularly from another half slip ring 8 on the other end of the first clip bar 5. In other words, the plane defined by the clip arms 1 and 2 is perpendicular to the planes defined by the S-shaped clip bars 5 and 6. The two opposing ends of the biological membrane 3 are rolled up, with one end wrapped around the first clip arm 1 and another end wrapped around the second clip arm 2 to form a receiving portion 10 that is defined by a generally U-shaped membrane sheath that appears to be sagging as it is supported by the clip arms 1 and 2. The length of the biological membrane 3 is about the same as the length of the circumference of the receiving portion 10 formed by combining the half slip rings 8 and 9, while the width of the biological membrane 3 is about the same as the length of the clip arms 1 and 2 (or can be extended out from the ends of the clip arms 1 and 2 by 1-2 mm).

An active surface layer 4 comprising a specific polypeptide or glucosaminoglycan capable of adhering and accumulating growth factors is furnished on the inner surface of the biological membrane 3 through a coupling agent. The inner surface of the membrane 3 is the surface that faces and contacts the blood vessel when in use. The specific polypeptide is a condensation product of 16 lysines (K16), glycine (G), arginine (R), asparagic acid (D), serine (S), proline (P) and cysteine (C). The glucosaminoglycan is hyaluronic acid, chondroitin sulfate, dermatan sulfate, heparin, acetyl heparin sulfate or keratan sulfate. The biological membrane 3 is prepared by crosslinking and fixing and eliminating antigens on porcine, bovine or sheep diaphragm, omental fat, pericardial membrane or enteric membrane. The metal clip is made of stainless steel or titanium alloy for medical applications.

This biological membrane 3 can be made from the following steps, utilizing natural durable soft tissues from animals:

1. Pretreatment: Initial sterilization is performed using broad spectrum, highly-effective and low-toxicity bacteriacides such as benzalkonium bromide, sodium azide and chlorhexidine, followed by eliminating impurities and trimming irregular portions.

2. Defatting: The fatty substances in the membrane 3 are extracted with organic solvents such as chloroform, acetone, ethyl acetate, diethyl ether, anhydrous alcohol or mixtures thereof.

3. Cross-linking and Fixation: The protein molecules in the membrane 3 are crosslinked and fixed using a fixative. The fixative is one or two reagents selected from among epoxides, diamides, diisocyanates and carbodiimides, which can easily undergo crosslinking with protein molecules. Epoxides are preferred, and the epoxide may be monocyclic epoxides

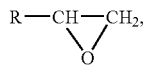

or bycyclic epoxides

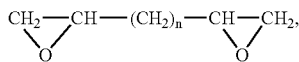

where $R=C_nH_{2n+1-}$, n=0-10.

4. Minimizing antigens: The active groups (such as —OH or —NH2 or —SH, etc.) at specific locations in the proteins of biological membrane 3 are closed by using an active reagent, and the specific hydrogen bonding on the spiral chains of the protein molecules of biological membrane 3 is replaced using a strong hydrogen bonding reagent. The activating reagent may be low molecular weight organic acid anhydrides, acyl chloride, acylamides or monocyclic oxides, and the strong hydrogen bonding reagent is a guanidine compound. The coupling agent may be a diamide or diacid anhydride or bycyclic oxide or other bifunctional reagent capable of undergoing a condensation reaction with —NH2 or —OH or —COOH, etc.

5. Surface modification: An active ingredient such as a specific polypeptide is deposited on the surface of the membrane 3 through coupling using a diamide, acid anhydride, epoxide or other bifunctional reagent capable of undergoing condensation with —NH$_2$, —OH, —COOH, etc., to form the active surface layer 4 on the surface of the membrane.

Finally, the two ends of the treated biological membrane 3 are fixed on the clip arms 1 and 2 of the metal clip, respectively, using a medical adhesive, thereby obtaining the aneurysm clip according to one embodiment of the present invention.

While the description above refers to particular embodiments of the present invention, it will be understood that many modifications may be made without departing from the spirit thereof. The accompanying claims are intended to cover such modifications as would fall within the true scope and spirit of the present invention.

What is claimed is:

1. An aneurysm clip, comprising:
    a biological membrane that is a natural animal tissue isolated from its host and having a substrate that has: (i) been fixed with crosslinking reagents, (ii) residual specific active groups in protein molecules of the substrate that have been blocked by at least one active reagent after fixation by the crosslinking reagents, (iii) specific conformation of protein molecules of the substrate altered by a reagent with strong hydrogen bonding power, and (iv) an active layer coupled thereto, the active layer including either a polypeptide or a glucosaminoglycan that has the ability to adhere growth factors after implantation;
    a metal clip having:
        a first clip bar and a second clip bar that are attached to each other in a biased manner;
        a first clip arm that extends from the second clip bar, and a second clip arm that extends from the first clip bar;
    wherein the biological membrane is coupled to the first and second clip arms in a manner that defines a curved receiving portion.

2. The clip of claim 1, wherein the membrane has opposing first and second ends, with each end defining a lumen, with the lumen of the first end of the biological membrane receiving the first clip arm, and the lumen of the second end of the biological membrane receiving the second clip arm.

3. The clip of claim 1, wherein the first clip arm extends in a plane that is perpendicular to the plane of the second clip bar, and the second clip arm extends in a plane that is perpendicular to the plane of the first clip bar.

4. The clip of claim 1, wherein the substrate is fixed by an epoxide, a diamide, a diisocyanate, or a carbodiimide.

5. The clip of claim 1, wherein the at least one active reagent to block specific active groups in the protein molecules of the substrate can be acid anhydrides, acryl chlorides, or acylamides.

6. The clip of claim 4, wherein the epoxide has a hydrocarbon backbone, that is water-soluble, and which does not contain an ether or ester linkage in its backbone.

7. The clip of claim 1, wherein the natural animal tissue is pericardium or peritoneum.

8. The clip of claim 1, wherein the reagent with strong hydrogen bonding power is a guanidine compound.

* * * * *